(12) United States Patent
Tunac

(10) Patent No.: US 8,258,125 B2
(45) Date of Patent: *Sep. 4, 2012

(54) HDL-BOOSTING COMBINATION THERAPY COMPLEXES

(76) Inventor: Josefino B. Tunac, Oxford, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/143,217

(22) Filed: Jun. 20, 2008

(65) Prior Publication Data

US 2008/0248070 A1    Oct. 9, 2008

(51) Int. Cl.
| | |
|---|---|
| A61K 31/585 | (2006.01) |
| A61K 31/70 | (2006.01) |
| A61K 31/535 | (2006.01) |
| A61K 31/44 | (2006.01) |
| A61K 31/355 | (2006.01) |
| A61K 31/35 | (2006.01) |
| A61K 31/34 | (2006.01) |
| A61K 31/19 | (2006.01) |
| A61K 31/195 | (2006.01) |

(52) U.S. Cl. ....... 514/175; 514/52; 514/168; 514/231.5; 514/332; 514/458; 514/460; 514/474; 514/557; 514/567; 514/568

(58) Field of Classification Search .................. 424/464, 424/400, 497; 514/557, 567, 568, 50, 175, 514/231.5, 168, 458, 474, 52, 332
See application file for complete search history.

(56) References Cited

U.S. PATENT DOCUMENTS

| | | | | |
|---|---|---|---|---|
| 3,262,850 | A | * | 7/1966 | Jones et al. .................. 514/568 |
| 3,674,836 | A | * | 7/1972 | Creger ............................ 560/61 |
| 3,773,946 | A | | 11/1973 | Creger |
| 3,930,024 | A | | 12/1975 | Creger |
| 4,231,938 | A | | 11/1980 | Monaghan et al. |
| 4,287,200 | A | | 9/1981 | Kawamatsu et al. |
| 4,346,227 | A | | 8/1982 | Terahara et al. |
| 4,444,784 | A | | 4/1984 | Hoffman et al. |
| 4,613,593 | A | | 9/1986 | Yamatsu et al. |
| 4,689,344 | A | | 8/1987 | Bar-Tana |
| 4,711,896 | A | | 12/1987 | Bar-Tana et al. |
| 4,814,354 | A | * | 3/1989 | Ghebre-Sellassie et al. . 424/440 |
| 5,260,440 | A | | 11/1993 | Hirai et al. |
| 5,273,995 | A | | 12/1993 | Roth |
| 5,354,772 | A | | 10/1994 | Kathawala |
| 5,756,344 | A | | 5/1998 | Onda et al. |
| 5,756,544 | A | | 5/1998 | Bisgaier et al. |
| 6,066,653 | A | | 5/2000 | Gregg et al. |
| 6,140,343 | A | | 10/2000 | DeNinno et al. |
| 6,197,786 | B1 | | 3/2001 | DeNinno et al. |
| 6,357,821 | B1 | | 3/2002 | Maj et al. |
| 6,502,653 | B1 | | 1/2003 | Balzer et al. |
| 6,506,799 | B1 | | 1/2003 | Dasseux |
| 6,511,985 | B1 | | 1/2003 | Ippen et al. |
| 6,534,088 | B2 | | 3/2003 | Guivarch et al. |
| 6,569,461 | B1 | * | 5/2003 | Tillyer et al. .................. 424/497 |
| 6,569,463 | B2 | | 5/2003 | Patel et al. |
| 6,589,969 | B1 | | 7/2003 | Tajima et al. |
| 6,600,045 | B2 | | 7/2003 | Damon et al. |
| 6,631,562 | B1 | | 10/2003 | Balzer et al. |
| 6,634,576 | B2 | | 10/2003 | Verhoff et al. |
| 6,679,545 | B1 | | 1/2004 | Balzer et al. |
| 7,390,504 | B2 | * | 6/2008 | Tunac ........................... 424/464 |
| 2001/0006655 | A1 | | 7/2001 | Chen et al. |
| 2002/0056206 | A1 | | 5/2002 | Pace et al. |
| 2002/0151536 | A1 | | 10/2002 | Davis et al. |
| 2002/0183305 | A1 | | 12/2002 | Davis |
| 2003/0045501 | A1 | * | 3/2003 | Bechtold ........................ 514/50 |
| 2003/0053981 | A1 | | 3/2003 | Davis et al. |
| 2003/0176501 | A1 | | 9/2003 | Tillyer et al. |
| 2003/0212137 | A1 | | 11/2003 | Cheng et al. |
| 2003/0224058 | A1 | | 12/2003 | Ryde et al. |
| 2004/0009961 | A1 | | 1/2004 | Borody |

OTHER PUBLICATIONS

Communication Pursuant to Article 96(2 EPC, dated Aug. 9, 2006; Application No. 04 810 579.5-2123; Applicant JJ Pharma, Inc.

* cited by examiner

*Primary Examiner* — Kevin E Weddington

(74) *Attorney, Agent, or Firm* — Young Basile Hanlon & MacFarlane, P.C.; Denise M. Glassmeyer

(57) ABSTRACT

A pharmaceutical composition including therapeutically effective amounts of at least one HMG-CoA reductase inhibitor present as a dyhydroxyacid salt and at least one additional therapeutic agent.

18 Claims, No Drawings

HDL-BOOSTING COMBINATION THERAPY COMPLEXES

RELATED APPLICATIONS

This application claims priority to U.S. application Ser. No. 10/983,836, filed Nov. 8, 2004, which claims priority from U.S. Provisional Patent Application No. 60/518,091 filed Nov. 7, 2003. The present invention relates to the use of water-soluble salts of dihydroxy open acid statins that are inhibitors of 3-hydroxy-3-methylglutaryl-coenzyme A (HMG-CoA) reductase in combination with at least one additional therapeutic agent.

BACKGROUND

Various medical conditions, including but not limited to certain forms of cancer, hepatic malfunctions, dementias such as Alzheimer's disease, and various lipid abnormalities can be advantageously treated using inhibitors of HMG-CoA reductase. It is also posited that various other diseases and medical conditions are related to pathways that utilize HMG-CoA reductase. Thus treatment regimens utilizing HMG-CoA reductase inhibitors are valuable and warranted.

In many instances, combination therapies employing two or more therapeutic compounds are required to adequately address the medical condition and/or physical effects secondary to the condition under treatment. Thus, HMG-CoA reductase inhibitors can be employed with various other therapeutic agents to address lipid abnormalities. Combining two lipid-lowering medications safely and effectively improves overall beneficial effect on all lipid abnormalities and reduces multiple coronary heart disease risk factors.

Coronary heart disease (CHD) is currently managed by various drug therapies that include HMG-CoA reductase inhibitors (collectively known as statins), as well as other compounds such as fibrates, bile acid sequestrants, niacin and the like. Of these drugs, statins are the most prescribed because they are effective in lowering total cholesterol and low-density lipoprotein cholesterol (LDL-C). It has been found that statins have a small to moderate effect on triglycerides and a minimal effect at raising high-density lipoprotein cholesterol (HDL-C) levels, the so-called "good cholesterol". While the National Cholesterol Education Program (NCEP) treatment guidelines recognize LDL-C as the primary target of therapy for prevention, it now focuses on HDL-C levels as a major risk factor. Moreover, the Adult Treatment Panel (ATP) of NCEP has now raised the HDL-C lower limit from 35 mg/dL to 40 mg/dL.

Statins are not effective at increasing HDL-C. However, various other materials such as fibrates can increase the level of HDL-C "good cholesterol." Combined statin and fibrate therapy is often imperative for the improvement of the serum lipid profile in patients with mixed hyperlipidemia. However, the potential risk of myopathy has limited the widespread use of such therapy. Current combination therapies recommend separate dosing to minimize peak dose interactions. Thus, dosing regimens can include weekly administration of a material such as a fibrate together with daily statin treatment. Other treatment regimens may include a fibrate prescribed in the morning and a statin prescribed at night to minimize peak dose interactions. Such dosing complexity can lead to compliance problems and less than desirable dose response in a patient.

Thus, it would be desirable to develop formulations of water-soluble salts of statin dihydroxy open acid and other suitable components having suitable effect on cholesterol, triglyceride, or related blood chemistries. It would also be desirable to provide a formulation of such materials in a single pill or dose form in order to address the overall lipid abnormalities. It would also be desirable to provide a dose form in which the water-soluble statin dihydroxy acid salt and other lipid addressing materials are present in a form that would enable formulation of a combination drug that can be administered at therapeutically effective low doses in order to eliminate undesirable side effects.

Similar dosing complexities exist in treating other medical conditions for which HMG-CoA reductase inhibitors can be utilized. Thus, it would be desirable to provide therapeutic compositions that combine HMG-CoA reductase inhibitors and other complementary agents in a single dose form for treating various illnesses and conditions that are moderated or controlled by HMG-CoA reductase.

SUMMARY

Disclosed herein is a therapeutically effective formulation involving a combination of an HMG CoA reductase inhibitor and at least one other therapeutic agent. The combined formulation is designed to improve the overall beneficial effect on all lipid parameters. The combined formulary can consist of a water soluble salt of a dihydroxy open acid statin and a water soluble salt of a fibrate.

DETAILED DESCRIPTION OF THE EMBODIMENTS

Currently used therapeutic agents addressing lipid abnormalities, particularly those occurring in coronary heart disease include, HMG Co-A reductase inhibitors. Other therapeutic agents addressing lipid abnormalities include, but are not limited to, fibrates, bile acid sequestrants, and niacin. Each of these materials is typically administered as monotherapies in which multiple materials are independently administered to address various lipid abnormalities. Disclosed herein is a pharmaceutical formulation in which at least two therapeutically effective entities are combined and can have the effect of reducing factors such as total cholesterol, LDL-C, triglycerides, and/or at increasing levels of HDL-C, popularly known as "good cholesterol".

In addition to use as therapeutic agents addressing lipid abnormalities, HMG-CoA reductase inhibitors have demonstrated efficacy in the treatment of certain forms of cancer as well as the potential for addressing symptoms of Alzheimer's disease.

Disclosed herein is a therapeutic combination that contains at least one therapeutically active form of an HMG CoA reductase inhibitor and at least one additional therapeutic agent that is a compound other than an HMG CoA reductase inhibitor. The additional therapeutic agent may be capable of addressing at least one lipid abnormality.

As defined herein, the term "lipid abnormality" is taken to mean a deviation in at least one of total cholesterol value, LDL-C, triglyceride, or HDL-C levels from that defined as normal or acceptable by the National Cholesterol Education Program. The currently accepted normal values are listed in Table I. It is understood that the materials utilized in the therapeutic combination are those that address at least one of the lipid abnormalities in a statistically acceptable number of individuals. Thus, the materials utilized in the therapeutic composition disclosed herein will address at least one of total cholesterol, HDL-C, LDL-C, and triglycerides. It is contemplated that the materials may address more than one of the aforementioned abnormalities as desired or required.

TABLE 1

Normal Serum Values (mg/dL) for Various Lipoprotein Materials as Defined by National Cholesterol Education Program

| RATING CATEGORY | LDL CHOL | HDL CHOL | TRI-GLYCERIDES | TOTAL CHOLESTEROL |
|---|---|---|---|---|
| Optimum | <100 | >60 | <100 | — |
| Near Optimum | 100-129 | 50-59 | 100-149 | <200 |
| Increased Risk | 130-159 | 41-49 | 150-199 | 200-239 |
| High Risk | 160-189 | 35-40 | 200-399 | >240 |
| Very High Risk | >190 | <35 | >400 | — |

It is contemplated that "addressing at least one lipid abnormality" will be evidenced by a positive trending resolution toward the desired value as defined by appropriate agencies and individuals. It is to be understood that the material of choice may exhibit effect on lipid and lipid-like materials even within the range defined as acceptable by the appropriate agency or individual and/or that defined in Table I.

It is contemplated a therapeutic agent capable of addressing at least one lipid abnormality can include at least one of peroxisome proliferator-activated receptor agonists, cholesterol ester transfer protein modifiers, either as inhibitor or agonist, long-chain carboxylic acids, long chain carboxylic ether compounds, and the like. Examples of such materials can include but are not limited to water soluble materials such as fibrates, niacin and insoluble or semisoluble materials such as bile acid sequestrants.

It is contemplated that the therapeutic agent is used in combination with a suitable HMG CoA reductase inhibitor. The HMG CoA reductase inhibitor in the composition can be present as its biologically active form.

The term "HMG CoA reductase inhibitor" as used herein is intended to include inhibitors of the 3-hydroxy-3-methylglutaryl co-enzyme A reductase pathways. In particular these include statins: a structural class of compounds that contains a moiety that can exist either as a 3-hydroxy lactone ring, or as the corresponding dihydroxy open acids.

All hydrates, solvates, and polymorphic crystalline forms of HMG-CoA reductase inhibitors having the above-described dihydroxy open moiety are included within the scope of the term "statin". Pharmaceutically acceptable salts and esters of the dihydroxy open acid statins are included within this term.

Statins inhibit HMG-CoA reductase in the dihydroxy open acid form. Compounds that have inhibitory activity for HMG-CoA reductase can be readily identified using assays well known in the art. Examples of such assays are described or cited in U.S. Pat. No. 4,231,938 at column 6. As disclosed herein, the HMG-CoA reductase inhibitor can advantageously be a dihydroxy open acid statin.

The term "dihydroxy open acid statin(s)" is intended to be defined as statins containing the dihydroxy open acid moiety including pharmaceutically acceptable salts and esters thereof. The phrases "dihydroxy open acid statin(s)," and "dihydroxy open statin(s)," and "pharmaceutically acceptable salts and esters thereof" are used interchangeably herein and are all intended to encompass the open acid and salt and ester forms of the open acid of the statin, unless otherwise indicated. All hydrates, solvates, and polymorphic crystalline forms are encompassed within the scope of the term "dihydroxy open acid statin(s)." In the broadest sense, any dihydroxy open acid statin or a pharmaceutically acceptable salt or ester thereof may be used in the present invention. The HMG CoA reductase inhibitor can be one derived from the lactone form having the general formula:

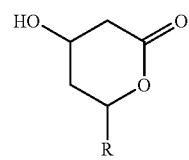

in which R is the statin chromophore of the respective compound. The HMG CoA reductase inhibitor compound employed herein is present as its biologically active form having the general formula:

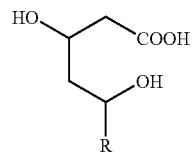

in which R is the statin chromophore for the respective compound. Non-limiting examples of statin chromophores include at least one of simvastatin, lovastatin, pravastatin, fluvastatin, atorvastatin, cerivastatin, pitavastatin, and rosuvastatin. The materials of choice generally exhibit water solubility.

As used herein "water solubility" is defined as the ability of at least a portion of the material to dissolve or be solubilized by water. Thus, examples of dihydroxy open acid statins that may be used with the present invention include, but are not limited to, dihydroxy open acid forms and pharmaceutically acceptable salts and esters of materials such as: lovastatin, simvastatin, pravastatin, fluvastatin, atorvastatin, cerivastatin, pitavastatin, rosuvastatin.

In the broadest sense, pharmaceutically acceptable salts of statin dihydroxy-acid include, but are not limited to, cation salts such as sodium, potassium, aluminum, calcium, lithium, magnesium, zinc, and tetramethylammonium, as well as those salts formed from amines such ammonia, ethylene diamine, n-methylglucamine, lysine, arginine, ornithine, choline, N—N' dibenzylethylenediamine, chloroprocaine, diethanolamine, procaine, N-benzylphenethylamine, 1-p chlorobenzyl-2 pyrrolidine-1'-yl-methylbenzimidazole, diethylamine, piperazine, morpholine, 2,4,4-trimethyl-2 pentamine, and tris(hydroxylmethyl)aminomethane, as well as pharmaceutically acceptable esters to include, but not be limited to, $C_{1-4}$ alkyl and $C_{1-4}$ alkyl substituted with phenyl, dimethylamino, and acetylamino. As used herein, the term "$C_{1-4}$alkyl" includes straight or branched aliphatic chains containing from one to four carbon atoms. Nonlimiting examples include straight or branched aliphatic chains such as, methyl, ethyl, n-propyl, n-butyl, iso-propyl, sec-butyl and tert-butyl.

It is contemplated that the dihydroxy open acid statin will be formulated for oral administration in a manner that allows for delivery of the dihydroxy open acid statin without its lactone counterpart. As desired or required, the dihydroxy open acid statin can be formulated to be delivered directly to the absorptive mucosa of the small intestine, thus allowing for absorption of the open acid statin into portal circulation, penetration by the open active statin into hepatocytes to achieve enhanced efficacy and systemic exposure consisting of open acid moieties. Without being bound to any theory, it is believed that maintaining the statin in its open acid form in the body reduces the potential for drug interactions between statins (whose metabolism is CYP3A4-mediated) and other active agents (that inhibit this CYP3A4 enzymatic pathway), thereby providing enhanced efficacy of the composition disclosed herein.

As disclosed herein, the pharmaceutical composition also includes at least one additional material exhibiting at least one anti-hypercholesterolemic effect. The material of choice can be lipid lowering compounds or agents having other pharmaceutical activities, or agents having both lipid lowering effects and other pharmaceutical activities. Suitable materials will be preferably water-soluble. Nonlimiting examples of additional active agents that can be advantageously employed in the formulation disclosed herein will be water soluble and can include HMG-CoA reductase inhibitors, squalene epoxidase inhibitors, squalene synthetase inhibitors (also known as squalene synthase inhibitors), acyl-coenzyme A, cholesterol acyltransferase (ACAT) inhibitors including selective inhibitors of ACAT-1 or ACAT-2, as well as dual inhibitors of ACAT-1 and ACAT-2, microsomal triglyceride transfer protein (MTP) inhibitors, probucol, niacin, cholesterol absorption inhibitors such as SCH-58235, also known as ezetimibe and 1-(4-fluorophenyl)-3(R)-3(S)-(4-fluorophenyl)-3-hydroxypropyl), 4(S)-4-hydroxyphenol (-2-azetidinone) described in U.S. Pat. Nos. 5,727,115 and 5,846,966, bile acid sequestrants, LDL, (low density lipoprotein) receptor inducers, platelet aggregation inhibitors (for example glycoprotein IIb/IIa fibrinogen receptor antagonists and aspirin. Human peroxisome proliferator activated receptor gamma (PPARγ) agonists may also be employed including the compounds commonly referred to as glitazones, for example troglitazone, pioglitazone, and rosiglitazone, and those compounds included within the structural class known as thiazolidinediones, as well as those PPARγ agonists outside the thiazolidinedione structure class, PPARα agonists such as clofibrate, fenofibrate, gemfibrozil, bezafibrate, and ciprofibrate, PPAR dual α/γ agonists, vitamin $B_6$ (also known as pyridoxine), Vitamin $B_{12}$ (also known as cyanocobalamin), folic acid in its water-soluble pharmaceutical salt or ester, such as sodium salt and the methylglucamine salt, anti-oxidant vitamins such as vitamin C and E and beta-carotene, beta-blockers, angiotensin II antagonists such as losartan, angiotensin converting enzyme inhibitors such as enalapril and captopril, calcium channel blockers such as nifedipine and diltiazem, endothelial antagonists, and the like. Other non-limiting examples of water soluble therapeutic agents include compounds associated with anti-retroviral therapies such as those employed in the treatment of AIDS infected patients to treat lipid abnormalities associated with such treatment. These may include HIV protease inhibitors such as indinavir, nelfinavir, ritinavir and saquinavir.

More particularly, it is contemplated that the therapeutic agent used in connection with the dihydroxy open acid salt of the suitable statin will include at least one of fibrates, bile acid sequestrants, and nicotinic acid or niacin. As used herein, "fibrates" refer to a class of lipid lowering drugs used to treat various forms of hyperlipidemia (elevated serum triglycerides) that may be associated with hypercholesterolemia. The fibrates of choice are water-soluble compounds having the effect of treating people with very high triglyceride levels through the lipoprotein lipase-mediated effect on lipolysis and by reducing triglyceride production in the liver. The fibrates of choice may also increase HDL-C by regulating apolipoprotein (apo)AI and (apo)AII gene expression. The fibrates of choice, in addition to alterations in plasma HDL-C levels, can induce emergence of large, cholesteryl ester-rich HDL. Fibrates can be defined as PPAR-alpha agonists (peroxisome proliferator activated receptor alpha agonists), including fibric acid derivatives and pharmaceutically acceptable salts and esters of such fibric acid derivatives, such as clofibrate, the ethyl ester of p-chlorophenoxyisobutyrate. Fibric acid derivatives lower the levels of triglyceride-rich lipoproteins, such as VLDL, raise HDL levels, and have variable effects on LDL levels. The effects on VLDL levels appear to result primarily from an increase in lipoprotein lipase activity, especially in muscle. This leads to enhanced hydrolysis of VLDL triglyceride content and an enhanced VLDL catabolism. Fibric acid agents also may alter the composition of the VLDL, for example, by decreasing hepatic production of apoC-III, an inhibitor of lipoprotein lipase activity. These compounds are also reported to decrease hepatic VLDL triglyceride synthesis, possibly by inhibiting fatty acid synthesis and by promoting fatty acid oxidation as a result of peroxisomal proliferation.

Fibrate derivatives include but are not limited to the salts of clofibrate, gemfibrozil, fenofibrate, ciprofibrate, and bezafibrate. The structure of each is represented below:

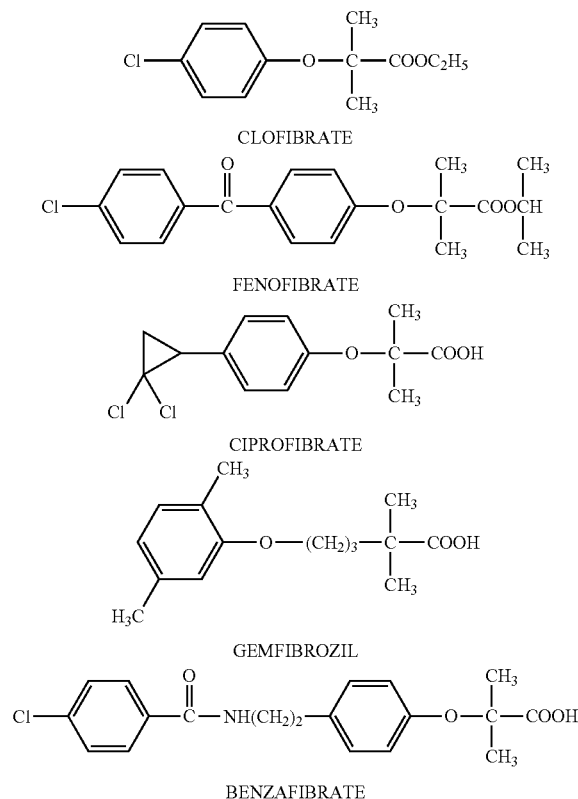

Fenofibrate is commercially available as Tricor capsules. Each capsule contains 67 mg of micronized fenofibrate. Fenofibrate regulates lipids. Fenofibric acid, the active metabolic of fenofibrate, lowers plasma triglycerides apparently by inhibiting triglyceride synthesis, resulting in a reduction of VLDL released into the circulation, and also by stimulating the catabolism of triglyceride-rich lipoprotein (i.e. VLDL). The recommended daily dose of fenofibrate is 67 mg.

Clofibrate is commercially available as Atromid-S capsules. Each capsule contains 500 mg of clofibrate. Clofibrate lowers elevated serum lipids by reducing the very low-density lipoprotein fraction rich in triglycerides. Serum cholesterol may be decreased. It may inhibit the hepatic release of lipoproteins (particularly VLDL) and potentiate the action of lipoprotein lipase. The recommended daily dose of clofibrate is 2 grams, administered in divided doses.

Gemfibrozil is commercially available as Lopid tablets. Each tablet contains 600 mg of gemfibrozil. Gemfibrozil is a lipid regulating agent that decreases serum trigylcerides and very low density lipoprotein cholesterol, and increases high density lipoprotein cholesterol. The recommended daily dose of Gemfibrozil is 1200 mg, administered in two divided doses.

Fibrates include PPAR-alpha agonists which may also act as agonists for PPAR-gamma and/or PPAR-delta subtypes. PPAR-alpha, PPAR-gamma and PPAR-delta agonists may be identified according to an assay described in U.S. Pat. No. 6,008,239, pharmaceutically acceptable salts and esters of PPAR-agonists are likewise included within the scope of this invention.

Other fibrates may be employed as desired or required. These include, but are not limited to, materials such as bezafibrate and ciprofibrate. The fibrate employed in the composition disclosed herein may be a water-soluble derivative of fenofibrate (2-[4-)4-chlorobenzoyl)phenoxy]-2-methyl-propionic acid-1-methylethyl ester. Fenofibrate is a prodrug that is essentially insoluble in water. Fenofibrate is typically absorbed and then hydrolyzed by tissue and plasma esterases to fenofibric acid, the active metabolite. It is this fenofibric acid that is the active species responsible for pharmacological activity of fenofibrate. In the composition disclosed herein, it is contemplated that the acid derivative of fenofibrate can be employed in connection with the dihydroxy acid salt of a statin or statins. In the broadest embodiment, suitable pharmaceutically acceptable salts of fibric acid shall include, but not be limited to, cationic salts such as sodium, potassium, aluminum, calcium, lithium, magnesium, zinc, and tetramethylammonium, as well as those salts formed from amines, such as ammonia, ethylenediamine, N-methylglucamine, lysine, arginine, ornithine, choline, N,N' dibenzylethylenediamine, chloroprocaine, diethanolamine, procaine, N-benzylphenethylamine, 3-P-chlorobenzyl-2-pyrolidone-1'-yl-methylbenzimidazole, diethylamine, piperazine, morpholine, 2,4,4-trimethyl-2-pentamine, and tris(hydroxymethyl)aminomethane, as well as pharmaceutically acceptable esters to include, but not be limited to, $C_{1-4}$alkyl and $C_{1-4}$alkyl substituted with phenyl-dimethylamino-N acetylamino groups.

The effects of fenofibric acid seen in clinical practice have been explained in vivo in transgenic mice and in vitro in human hepatocyte cultures by the activation of peroxisome proliferator activated receptor alpha (PPARα). Through this mechanism, fenofibrate increases lipolysis and elimination of triglyceride-rich particles from plasma by activating lipoprotein lipase and reducing production of apoprotein C-III (an inhibitor of lipoprotein lipase activity). The resulting fall in triglycerides produces an alteration in the size and composition of LDL-C from small, dense particles (which are thought to be atherogenic due to their susceptibility to oxidation), to large buoyant particles. These larger particles demonstrate greater affinity for cholesterol receptors and are catabolized rapidly. It is also contemplated that activation of PPARα also induces an increase in the synthesis of apoproteins A-I, A-II, and HDL-C.

The therapeutic agent can also be a bile acid sequestrant. Bile acids, the major components of bile, are produced in the liver and are created from cholesterol. Once secreted into the small intestine, the majority of bile acids are reabsorbed and neutralized. The body must then make up for this bile acid loss by manufacturing more, thereby using up more of the cholesterol supplied. Bile acid sequestrants bind bile acids in the intestine, resulting in an interruption of the reabsorption of bile acids thereby reducing the reabsorption efficiency from an amount of approximately 90% to levels lower than this. Nonlimiting examples of available bile acid sequestrants include, but are not limited to, cholestyramine, colestipol, described in U.S. Pat. No. 3,383,281 and colesevelam.

These and other suitable materials, when orally administered to a mammalian host, form complexes with bile acid conjugates in the intestine and are effective in blocking resorption of bile acids from the intestine. The compound and sequestered bile acids are subsequently excreted from the body in fecal matter thereby increasing the rate at which bile acids are eliminated from the body. Other factors being equal, an increase in the rate at which bile acids are eliminated from the body tends to lower plasma cholesterol level by accelerating the conversion of cholesterol to bile acids in order to maintain a constant supply of bile acids. A portion of the cholesterol for this increased synthesis of bile acids is supplied by removal of cholesterol from the blood plasma.

Orally administered single compound bile acid sequestrants are typically positively charged resins that bind to negatively charged bile acids in the intestine. Because the resins cannot be absorbed from the intestine, they are excreted carrying the bile acids with them. Conventional use of such resins accomplishes a lowering in serum cholesterol levels of 20% or less. As bile acid sequestrant materials are never absorbed into the body, they have few systemic side effects. However, bile acid binding resins typically come as granules that must be thoroughly mixed with water or juices and taken two to three times daily. These resins may also bind to other medications being taken. Thus a carefully planned dosing regimen must be developed by the patient and physician in order to obtain maximum therapeutic benefit and avoid adverse interactions with other medications.

It has been found, quite unexpectedly, that bile acid sequestrants used in concert with HMG CoA reductase inhibitors such as dihydroxy open acids salts of statins can exhibit increased potency in lowering serum cholesterol levels, particularly in patients with markedly !elevated plasma levels of LDL-C. It has been found, quite unexpectedly, that formulations containing bile acid sequestrants and dihydroxy open acid salts of statin as formulated herein exhibit synergistic actions to lower LDL-C by levels approaching 50 percent, while raising HDL-C by amounts between 10 and 20 percent. The performance can be further enhanced, particularly with regard to elevation of the HDL cholesterol levels when the formulation is further compounded with nicotinic acid.

Nicotinic acid also known as niacin or 3-pyridine carboxylic acid can be utilized in connection with the dihydroxy open acid salt of a statin in anticholesterolemic applications. Therefore, it has been known that B complex vitamins, such as nicotinic acid or niacin, when utilized in high doses, can lower the rate of cholesterol synthesis. Niacin can have a variety of effects on lipid metabolism. It raises HDL-C levels by as much as 30 to 35 percent, both by reducing lipid transfer of cholesterol from HDL-C to VLDL, and by delaying HDL-C clearance. Another favorable property of nicotinic acid or niacin is a reduction in plasma fibrinogen levels. Nicotinic acid is effective in patients with hypercholesterolemia and in combined lipidemia associated with normal and low levels of HDLC hypoalphalipoproteinemia). Typically, the HDL-C raising properties of nicotinic acid when used alone occur with dosages of 1 to 1.5 grams/day and the VLDL and LDL lowering effects are typically seen with higher doses (3 grams/day for example).

While niacin may sound like a perfect cholesterol-lowering drug, the frequency of minor but poorly tolerated side effects greatly limits its usefulness. Intense flushing sensations, nausea, and bloating are the most common patient complaints. While these effects can be mitigated by starting on a very low dose and slowly titrating to a higher effective dose, this process is tedious and not always fully satisfactory or effective. As with statin drugs, liver function must be monitored by periodic testing. Presentation of gout and gout-like symptoms in a certain percentage of the patient population probably indicates that niacin should be avoided. Nicotinic acid is available in several formulations that include immediate-release and sustained release formulations such as Niacore® and Niaspan®.

The various compounds and formulations function to affect serum cholesterol through various pathways. While fibrates and niacin have been proposed as therapies to raise HDL-C, fibrates raise HDL-C levels by an average of 5 to 30 percent (predominantly in the HDL-3 subfraction). The fibrates, particularly gemfibrozil and fenofibrate, appear to raise HDL levels by activating PPARα, which in turn enhances expression of HDL-regulating genes apoliproteins, A-I and A-II, lipoprotein lipase, and ABA 1. Niacin appears to reduce hepatic removal of the HDL apolipoprotein A-1 and hepatic lipase activity resulting in higher levels of HDL-C and, HDL2 subfraction. Heretofore, when such materials were used in combination therapy with statins, both statin and added therapeutic agent were hydrophobic materials. Prior to 1987, the lipid-lowering regimen (armamentarium) was limited essentially to low saturated fat and cholesterol diet, bile sequestrants such as cholestyramine and colestipol, nicotinic acid (niacin), fibrates, and probucol. Unfortunately, all of these treatments had limited efficacy or tolerability or both. Today the most frequently described class of cholesterol lowering drugs, the HMG-CoA reductase inhibitors or statins, act by inhibiting an enzyme that plays all important role in cholesterol synthesis. Statins have functioned well in decreasing the level of LDL-C and have demonstrated a corresponding decrease in coronary heart disease and total mortality. Reductions in myocardial infarctions, revascularization procedures, stroke, and peripheral vascular disease have also been demonstrated. The statins have also been widely accepted as the easiest of the cholesterol lowering drugs to use, as their response rate is highly predictable, and their side-effect rate is low. Occasionally aches or nausea are the most common reasons for stopping these drugs. However, severe muscle or liver inflammation can occur and can progress to myalgias, myopathy and/or life threatening rhabdomyolyis. Thus, these drugs must be closely monitored.

Introduced in 1987, lovastatin was the first statin based HMG-CoA reductase inhibitor. A similar agent, pravastatin, followed in 1991, along with simvastatin, a semisynthetic compound consisting of lovastatin plus an extra methyl group. In addition, there are now a variety of totally synthetic HMG-CoA reductase inhibitors, including fluvastatin, atorvastatin, and rosuvastatin. The basic material, lovastatin, is a white, lipophilic, nonhygroscopic crystalline powder that is insoluble in water (i.e., lipophilic) and sparingly soluble in ethanol, methanol, and acetonitrile. Lovastatin, an inactive lactone, is a prodrug that is metabolically transformed to the corresponding (beta)-hydroxy acid. This is the active metabolite that inhibits HMG-CoA reductase. Lovastatin, as with simvastatin, atorvastatin, and cerivastatin, are all substrates of CYP3A4, and are extensively metabolized on first pass through the liver. On the other hand, hydrophilic statins, like fluvastatin and pravastatin, are metabolized by CYP2C9 and pravastatin, not significantly metabolized by CYP, are comparatively devoid of incidence of myalgias, myopathy, or life-threatening rhabdomyolysis.

Optimal LDL-C levels have been set at 100 mg/dL and 115 mg/dL for high risk patients by US and European guidelines respectively. To achieve these therapeutic target values for LDL-C, statins have become a mainstay in the treatment of hyperlipidemia. These statements are recommended as first-line pharmacological therapy in the majority of hyperlipidemic patients at increased risk of initial or recurrent manifestations of coronary heart disease (CHD).

As discussed herein, it is contemplated that atherosclerosis underlies most coronary artery disease and thus contributes to a major cause of morbidity and mortality of modern society. High levels of LDL-C (i.e. above 180 mg/dL) and low levels of HDL-C (below 35 mg/dL) have been shown to be important contributors to atherosclerosis. Cholesterol and TG are part of lipoprotein complexes in the bloodstream. These complexes can be separated by an ultracentrifugation into HDL-C, LDL-C, intermediate density lipoprotein (IDL) cholesterol, and very low density lipoprotein (VLDL) cholesterol fractions. Cholesterol and TG are synthesized in the liver, incorporating into VLDL, and released into the plasma. High levels of total-C, LDL-C, and apolipoprotein B (apo-B), a membrane complex for LDL-C are considered to promote atherosclerosis, and decreased levels of HDL-C and its transport complex, apolipoprotein A. Cardiovascular morbidity and mortality can vary directly with the level of total-C and LDL-C and inversely with the level of HDL-C.

Atherosclerosis is a slowly progressive disease characterized by the accumulation of cholesterol within the arterial wall. The atherosclerotic process begins when LDL-C becomes trapped within the vascular wall. Oxidation of the LDL-C results in the bonding of monocytes to the endothelial cells lining the vessel wall. These monocytes are activated and migrate into the endothelial space where they are transformed into macrophages, leading to further oxidation of LDL-C. The oxidized LDL-C is taken up through the scavenger receptor on the macrophage leading the formation of foam cells. A fibrous cap is generated through the proliferation and migration of arterial smooth muscle cells, thus creating an atherosclerotic plaque. Lipids depositing in atherosclerotic legions are derived primarily from plasma apo B containing lipoproteins. These include chylomicrons, LDL-C, IDL, and VLDL. This accumulation forms bulky plaques that inhibit the flow of blood until a clot eventually forms, obstructing an artery and causing a heart attack or stroke.

LDL-C and HDL-C are the major cholesterol carrier proteins. LDL-C is responsible for the delivery of cholesterol from the liver, where it is synthesized or obtained from dietary sources to extrahepatic tissues in the body. HDL-C is responsible for "reverse cholesterol transport" from extrahepatic tissues to the liver where it is catabolized and eliminated.

Thus, while statins used independently have been recommended as first-line pharmacological therapy in the majority of hyperlipidemic patients at increased risk of initial or recurrent manifestations of coronary heart disease, the use of statins in clinical practice has achieved observed reductions in all LDL-C levels that are significantly less than those theoretically obtainable. The exact reason for this disappointing achievement is not known. However, it is theorized that many physicians are reluctant to titrate up statin treatment at the high doses because of known or perceived issues of tolerability and/or safety. Reluctance can also be attributed to perception that the highest statin dosages lack sufficient efficacy in the most severe dyslipidemias. In some surveys, of risk factor management of patients with established coronary heart disease, it is believed that only half of those patients receiving lipid-lowering statin therapy have attained recommended lipid treatment goals.

As indicated previously, no single drug, such as the statins, as yet addresses all lipid abnormalities. Various combination therapies, particularly combination therapies employing statin and fibrates that are complementary and additive have been proposed to address overall lipid abnormalities. As indicated previously, however, statins and compounds such as fibrates must be dosed individually on specific and complementary dosing regimens to ensure maximum and patient safety. While statins inhibit HMG CoA reductase, fibrates work on a different mechanism by activating peroxisome proliferator-activated receptor-alpha 1 (PPARα1) in the liver thereby improving the plasma transport rates of several lipoproteins. Other anti-atherothrombotic effects of fibrates include the inhibition of coagulation and enhancement of fibrinolysis, as well as the inhibition of inflammatory mediators involved in atherogenesis.

While the statin/fibrate therapy regimen has been proposed in situations where monotherapy does not achieve lipid targets or is impractical, statin-fibrate combination therapies can be difficult to administer and maintain even though these combination therapies can substantially reduce LDL-C and triglyceride and increase HDL-C levels. Current statin-fibrate combination therapies strongly recommend separate dosing of the two drugs, for example, weekly administration of fibrate and daily statin treatment or fibrates prescribed in the morning and a statin at night to minimize peak dose interactions. In contrast, it has been found, quite unexpectedly that the formulation disclosed herein containing a dihydroxy-open acid statin salt in combination with a fibrate, such as a water-soluble fibrate, can be administered in a single dose form to achieve significant decreases in LDL-C and trigylcerides and, most importantly, increases in HDL-C levels.

The instant pharmaceutical combination comprised a water-soluble HMG-CoA reductase inhibitor in combination with an additional water-soluble therapeutic material capable of administration in a single pharmaceutical dosage formulation containing both materials. The instant pharmaceutical combination is understood to include all these regimens. Administration in these various ways are suitable for the present invention as long as the beneficial pharmaceutical effect of the HMG-CoA reductase inhibitor and other therapeutic agent are realized by the patient at substantially the same time. Such beneficial effect is preferably achieved when the target blood level concentrations of each active drug are maintained at substantially the same time. It is contemplated that the materials be co-administered concurrently on a once-a-day dosing schedule; however, varying dosing schedules, such as once, twice or more times per day is also encompassed herein. It is contemplated that a single dosage formulation will provide convenience for the patient, which is an important consideration especially for patients who already have coronary heart disease and may be in need of multiple medications.

The term "patient" includes mammals, especially humans, who take an HMG-CoA reductase inhibitor in combination with another therapeutic agent for any of the uses described herein. Administering of the drug combination to the patient includes both self-administration and administration to the patient by another person.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing water-soluble HMG-CoA reductase inhibitor in combination with another water soluble therapeutic agent with a variety of factors including type, species, age, weight, sex, and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together should also be taken into account.

As used herein, a suitable dose form can be any modality that can delivery the active ingredients to the user in a manner suitable for uptake by the user. Thus, it is contemplated that the dose form can be an oral dose form, an implantable form, time released form, or the like. As articulated further, it is contemplated that the dose form will be an oral dose form. Dosage amounts per dose form will vary depending upon factors including, but not limited to, standard atherosclerotic disease factors, compound potency, and the like. It is also contemplated that the active drug may be administered in divided doses, for example, from one to four times daily, as desired or required. However, a single daily dose of the active compounds can be preferable in many applications.

Non-limiting examples of standard atherosclerotic disease factors that can be used in determining dosing include known risk factors such as hypertension, smoking, diabetes, low levels of high density lipoprotein (HDL), cholesterol, and a family history of atherosclerotic cardiovascular disease. Published guidelines for determining those who are at risk of developing atherosclerotic disease can be found in various sources such as the National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No. 93-3095 (September 1993 abbreviated version; Expert Panel on Detection, Evaluation, and Treatment of High Blood Cholesterol in Adults, Summary of the second report of the National Cholesterol Education Program (NCEP) Expert Panel on Detection, Evaluation, and Treatment of High Blood Cholesterol in Adults (Adult Treatment Panel II), JAMA, 1993, 269, pp. 3015-23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The active drug compounds employed in the instant therapy can be administered in various oral forms including, but not limited to, tablets, capsules, pills, powders, granules, elixirs, tinctures, suspensions, syrups, and emulsions. It is contemplated that the active drug compounds can be delivered by any pharmaceutically acceptable route and in any pharmaceutically acceptable dosage form. These include, but are not limited to the use of oral conventional rapid-release, time controlled-release, and delayed-release pharmaceutical dosage forms. The active drug components can be administered in a mixture with suitable pharmaceutical diluents, excipients or carriers (collectively referred to herein as "carrier" materials suitably selected to with respect to the intended form of administration. As indicated, it is contemplated that oral administration can be effectively employed.

Thus, tablets, capsules, syrups, and the like as well as other modalities consistent with conventional pharmaceutical practices can be employed.

In instances in which oral administration is in the form of a tablet or capsule, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Where desired or required, the active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

It is also contemplated that the active drugs may be delivered by the use of monoclonal antibodies as individual carriers to which the compound molecules are coupled. The active drug may also be coupled with soluble polymers such as targetable drug carriers. Non-limiting examples of such polymers can include polyvinyl-pyrrolidone, pyran copolymer, polyhydroxy-propyl-methylacrylamide-phenol, polyhydroxy-ethyl-aspartamide-phenol or polyethyleneoxide-polylysine substituted with palmitoyl residues. Furthermore, the active drugs may be coupled to a class of biodegradable polymers useful in achieving controlled release of a drug, for example polylactic acid, polyglycolic acid, copolymers of polylactic and polyglycolic acid, polyepsilon caprolactone, polyhydroxybutyric acid, polyorthoesters, polyacetals, polydihydropyrans, polycyanoacrylates, and crosslinked or amphipathic block copolymers of hydrogels.

Once administered, the active drugs work on the hepatic metabolism in various manners. Hepatic metabolism is served by a superfamily of oxygenases known as Cytochrome P 450s. These enzymes add a functional group to a drug, chemical or endogenous molecule to increase at least one of polarity, excretion from the body or interaction with similar enzymes. The most distinguishing characteristic of the Cytochrome P450 family is its great diversity and ability to react with almost any chemical species. The superfamily, referred to as the CYP enzymes, is subdivided according to the degree of homology in the amino acid sequences. Families are further divided into subfamilies, which are designated by a letter after the number, examples of these include CYP2C and CYP2D subfamilies. Members of each family typically have more than 55% homology with one another. Finally, individual members are given an additional number (for example CYP3A4) to identify a specific enzyme pathway. Over 70 CYP families have been identified to date of which 14 are known to occur in all mammals. Of the 26 mammalian sub families, the CYP2C, CYP2D, and CYP2A sub families are involved in the metabolism of most clinically relevant drugs.

The CYP3A sub family, like CYP2D6, is involved in the metabolism of a large number of drugs and other chemicals and is involved in many drug-drug and drug-food interactions. It is the most abundant of all the Cytochrome P450s in the human liver with enzyme amounts of 25 to 28% being common and amounts ranging as high as 70% being found in certain instances. Additionally, CYP3A is widely expressed throughout the gastrointestinal tract, kidneys and lungs. More than 150 drugs are known substrates of CYP3A4, the major CYP3A isozyme, including many of the opiate analgesics, steroids, antiarrhythmic agents, tricyclic antidepressants, calcium-channel blockers, macrolide antibiotics and certain of the statins.

As indicated previously, statins are associated with two uncommon but important side effects, namely a symptomatic elevation in liver enzymes and skeletal muscle abnormalities. These skeletal abnormalities can range from benign myalgias to myopathy exhibiting a tenfold elevation in creatine kinase with muscle pain or weakness. The abnormalities can also range to life-threatening rhabdomyolysis. The incidents of myopathy in patients taken statins alone is estimated to be 0.1 to 0.2% of the treated population. Rhabdomyolysis is lower than that.

Myopathy is most likely to occur when statins are administered with other drugs or chemicals that compete with the statin through the Cytochrome P450 (CYP3A4) enzyme system thereby elevating concentrations of statin to the toxic range. Thus, there has been reported an incidence of muscle disorder increase over tenfold when statins are administered with other therapeutic materials such as the fibrate, gemfibrozil, niacin, and the like. Adverse myopathies have also increased when statins are administered with erythromycin, itraconazole, cyclosporine, and diltiazem. Also, various substances found in grapefruit juice, green tea, and other foods are potent inhibitors of CYP3A4 and are known to be responsible for many drug interactions.

Without being bound to any theory, it is believed that myopathy is a direct consequence of HMG CoA reductase inhibition and is dose dependent. As the statins inhibit HMG CoA reductase, a variety of metabolic intermediates required for post-translational modification of a variety of regulatory proteins which are generated in the process of cholesterol synthesis are also depleted. Non-limiting examples of such regulatory proteins include mevalonate, ubiquinone, farnesol, and geranylgeraniol. The depletion of such metabolic intermediates has been postulated to potentially play a roll in statin-associated myotoxicity. Additionally, lipophilic statins are more readily able to enter skeletal muscle and accumulate than the non-lipophilic or hydrophilic statins. While highly lipophilic lactone pro drugs, such as lovastatin and simvastatin, are highly extracted by the hepatic tissues, their corresponding dihydroxy acid forms are hydrophilic and exhibit poor tissue penetration.

To further illustrate the present invention, reference is made to the following examples. These examples are set forth for purposes of illustration and are not considered limitative of the present invention.

EXAMPLE 1

In order to prepare a suitable HMG CoA reductase inhibitor, the material lovastatin was prepared. Lovastatin was produced during the fermentation process, for example by *Aspergillus terreus* ATCC 20542. Thus, using a suitable fermentation medium, a fermentor and fermentation conditions, the microorganism produce the compound which was primarily localized in the mycelia. In this regard, at harvest, the fermentation broth was centrifuged or filtered to recover the mycelial cake; the filtrate or supernatant did not contain the drug and thus was discarded.

After the broth was transferred to the holding tank, the pH of the broth was adjusted to 2.0 by adding HCl (about 0.75-1.0% of concentrated HCl by volume of broth). The HCl was added slowly while stirring.

The drug in the mycelial cake is extractable with an organic solvent. Preliminary data indicate that solvent extraction of the drug is more efficient with a dried mycelial cake than with a wet cake. In this regard, the filtered wet cake is dried prior to solvent extraction. Drying of the mycelial cake may be accomplished by simple air drying or by the aid of heat (e.g., sludge dryer). The color of the mycelia cake turns from tan to dark brown as it dries. Completeness of drying is decided by physical inspection, where there is no obvious moisture present in the sample.

The drug lovastatin is soluble in most organic solvents (e.g., methanol, acetone, ethyl acetate, methylene chloride, methylethylketone, etc.). For purposes of this process, methylethylketone (MEK) was employed for extracting the drug from the dried mycelial cake.

The dried mycelial cake was transferred to a stainless steel holding tank. To 1 part of the dried mycelial cake, about 4.0 parts MEK (e.g., 1 kg of dried mycelial cake: 4.0 liters or 1 gal of MEK) was added.

The dried mycelial cake can be soaked in MEK for at least overnight, with occasional stirring, to allow for ample extraction of the drug. After a certain period of soaking, the mixture can be filtered and the solvent extract recovered. The spent cake was rinsed with 2 parts fresh MEK and the MEK extracts were pooled.

The MEK extract contained crude lovastatin along with other extraneous compounds. The extract was concentrated, in vacuo, into an oily substance, using a thin film (e.g., Luwa) evaporator. To the oily concentrate, a filter aid (e.g., diatomaceous earth) was added at about 1.0% by weight of the volume of the pooled MEK extract. The filter aid was mixed into the oil until it turns into a dry solid mixture. The residual MEK was evaporated by air drying. To the dried mixture, 30% (by weight) of powdered activated carbon (e.g., Calgon's Colorsorb) was added and the admixture was mixed thoroughly.

The carbon-sample mixture was slurried into ethylacetate (e.g. about 2-4 parts by weight of carbon-sample mixture/volume ethylacetate).

Purification can be accomplished by any means such as a chromatographic system for the purification of lovastatin involving carbon and activated bauxite in the manner as follows:

The ethylacetate slurry was poured on top of a chromatographic column and eluted with ethylacetate. The activated carbon in the slurry adsorbs the extraneous color (e.g., brownish red color), and the activated bauxite in the column further adsorbs miscellaneous impurities.

The polypropylene column (1.0' diameter×4.0' height) was inspected for cleanliness and dryness. A glass wool or synthetic fiber filter lining was placed at the bottom of the column. The column was derived using three kilograms each of the different column components (e.g., filter aid, activated carbon, activated bauxite). Filter aid was added first, compressed by tapping. Activated carbon (e.g., Colorsorb) was then added, and the column tapped to compress. The activated bauxite was added, followed by another layer of filter aid. After the column was packed, the ethylacetate slurry was poured into the head-space of the column. The solvent was allowed to drain to the top of the carbon mixture at the top of the column. Three kilograms of additional filter aid (diatomaceous earth) was added to the top of the column to layer or "seal" off the carbon mixture.

Add batches of 20-L ethylacetate were added to elute the column, each time allowing the solvent to drain on top of the column before adding the next 20 liter batch. The eluate was recovered separately and the volume recovered was recorded. Each eluate was assayed for drug content and recorded below. Fresh ethylacetate was fed or added to the column until the entire drug has been eluted.

The rich-cut fraction of ethylacetate eluted from the chromatographic column is largely pure lovastatin. Although the drug is soluble in most organic solvents, if it is concentrated enough it precipitates in cold ethylacetate and can be washed with hexane or petroleum ether.

The ethylactate eluate was concentrated, in vacuo. Concentration may be carried out in a round flask evaporator or with a thin film (e.g., Luwa) evaporator.

As the ethylacetate was evaporated, crystals of lovastatin were formed. As crystals are formed, the concentrated solution was transferred in a cold room.

The concentrated solution was refrigerated for 1-3 days to complete the crystallization process. The wet crystals were harvested by filtration. The filtrate or mother liquid was recovered and the volume is recorded. The mother liquid may be further processed to recover additional drug.

Hexane was added to the crude crystals to wash off any residual color to observe white crystals. The hexane was removed by filtration and is recovered and distilled.

The lovastatin crystals were allowed to air dry to remove residual hexane and the crystals were recovered. The resulting crystals were the lactone compound form of lovastatin.

EXAMPLE 2

Salts of lovastatin can be prepared in the following manner:

The lactone compound isolated in Example 1 is conveniently transformed in to the dihydroxy-acid salts when hydrolyzed with bases such as NaOH or KOH to yield the corresponding sodium and potassium salts, respectively. The use of bases with the pharmaceutically acceptable cations affords salts of these cations.

A 10-gm lovastatin crystal isolated from Example 1, and a molar equivalent of NaOH were added while stirring at room temperature. After the mixture turns into a solution, it was taken to dryness in vacuo to yield the sodium salt of the free acid form hereinafter referred to as Compound I.

EXAMPLE 3

Preparation of the sodium salts of fibric-acid and niacin. The starting materials, fenofibrate, bezafibrate, and niacin are purchased from Sigma Chemicals (St. Louis, Mo.). To about 50 ml of ethanol 10-gm fenofibrate crystals, and a molar equivalent of NaOH are added while stirring at room temperature. After the mixture turns into a solution, it is taken to dryness in vacuo to yield the sodium salt of the free acid form of fenofibrate hereinafter referred to as Compound II.

In like manner, sodium salts of bezafibrate (Compound III) and niacin (Compound IV) are prepared using one equivalent of sodium hydroxide.

EXAMPLE 4

Evaluation of antilipidemic property in animal. Golden Syrian hamster, 8-wk old (85-100 g) (Bio®F1B, Bio Breeders, Inc., Watertown, Mass.) was the animal model chosen for this study because of its similarities with humans in lipoprotein metabolism and atherosclerosis Moreover, the hamster has plasma cholesteryl ester transfer protein (CETP) similar to humans. Dietary fat saturation affects apolipoprotein gene expression and high-density lipoprotein size distribution in golden Syrian hamsters.

The animals housed four per cage were fed Kaytee Supreme Fortified Hamster diet (Kaytee Products, Inc. Chilton, Wis.), with one part ratio of Heath High Energy suet (Heath Mfg., Cooperville, Mich.); water ad libitum. The animals were fed this diet for 1 week, and then given the drug treatment for a 2-week duration. Drugs were administered by daily oral gavage using 4:6 PEG/Cremaphore suspension vehicle for the water-insoluble drugs (e.g., atorvastatin, lovastatin, simvastatin, and the fibrates); the water-soluble drugs (dihydroxy-acid salts, pravastatin) were dissolved in water. Equivalent doses, based on a 70 kg man, were administered in the hamster. For example, a "10-mg dose" means 10 mg/70 kg (0.143 mg/kg). Thus, the calculated final dose for a 100-gm hamster is 0.143 mg as well (0.143 mg/100-gm hamster X a factor of "10"), formulated in a 0.25 ml solution for oral gavage administration. Each test substance is administered to 2-3 animals; control animals did not receive the drug and were used as reference. Body weights were recorded prior to drug administration and every other day during the test duration.

At termination, blood was collected from anesthetized hamsters and the serum is separated by centrifugation. Total serum cholesterol was assayed using the Hitachi Diagnostics enzymatic kit for the determination of total cholesterol, LDL cholesterol, HDL cholesterol, and triglyceride (Analysis performed by: Lipid Analysis, Inc., Springfield, Ill.).

TABLE 2

Comparison of antilipidemic activity of the dihydroxy-acid salt (Compound I and the currently marketed statins in a hamster animal model.

| | % Decrease On: | | | | | | | |
|---|---|---|---|---|---|---|---|---|
| | Total Cholesterol Equivalent Dose (mg) | | LDL-C Equivalent Dose (mg) | | HDL-C Equivalent Dose (mg) | | Triglyceride Equivalent Dose (mg) | |
| Drug | 160 | 8 | 160 | 8 | 160 | 8 | 160 | 8 |
| I | 40.7 | 30.3 | 29.2 | 41.4 | 32.2 | 25.2 | 33.7 | 28.6 |
| Lipitor (Atorvastatin) | 43.0 | 28.6 | 54.4 | 28.5 | 30.7 | 33.3 | 53.0 | 35.8 |
| Mevacor (Lovastatin) | 36.6 | 19.4 | 54.4 | 22.4 | 26.7 | 20.4 | 34.4 | 21.8 |
| Pravachol (Pravastatin) | 23.0 | 22.4 | 33.3 | 29.9 | 17.3 | 20.4 | 25.9 | 18.8 |
| Zocor (Simvastatin) | 40.7 | 9.5 | 54.4 | 5.4 | 30.7 | 12.6 | 43.0 | 23.4 |

The dihydroxy-acid salt (Compound I) was found to be readily soluble in water and was compared against the currently marketed cholesterol lowering drugs (Lipitor, Mevacor, Zocor, and Pravachol) for antilipidemic profile. Compound I was found to be comparable with Lipitor in lowering total cholesterol and trigylcerides, and better than Lipitor in lowering LDL-C particularly at 8 mg dose (Table 2).

TABLE 3

Comparison of antilipidemic activity of Compound I vs Lipitor in a hamster model.

| | % Decrease On: | | | | | | | |
|---|---|---|---|---|---|---|---|---|
| Equivalent Dose | Total Cholesterol | | LDL-C | | HDL-C | | Triglyceride | |
| (mg) | Lipitor | I | Lipitor | I | Lipitor | I | Lipitor | I |
| 5.0 | — | 14.8 | — | 14.7 | — | 5.6 | — | 4.5 |
| 10.0 | 18.2 | 12.6 | 17.9 | 23.7 | 20.7 | 12.4 | 5.0 | 6.8 |
| 20.0 | 12.3 | 20.9 | 8.9 | 22.4 | 15.9 | 20.7 | 4.8 | 23.6 |

A repeat side-by-side comparison between Compound I and Lipitor, this time at 5-20 mg dose range confirmed the effectiveness of Compound I in decreasing LDL-C. Moreover, Compound I was effective at a dose as low as 5 mg (Table 3).

TABLE 4

Antilipidemic activity of Compound I in combination with one of Compounds II, III, and IV.

| Drug/Equivalent Dose | | | % Decrease or Increase (i) On: | | | |
|---|---|---|---|---|---|---|
| | | | CHOLES | TRIG | HDL-C | LDL-C |
| I (10 mg) | +Niacin | (150 mg) | 5.6 | 22.3i | 1.18 | 8.9 |
| | | (300 mg) | 9.3 | 26.2i | 13.8 | 16.6 |
| | | (600 mg) | 12.3 | 10.9i | 17.2 | 19.3 |
| | +II | (50 mg) | 10.3 | 47.9 | 8.0i | 13.2 |
| | | (100 mg) | 12.8 | 63.9 | 3.4i | 3.1 |
| | | (200 mg) | 20.4 | 73.4 | 3.4i | 33.6 |
| | +III | (50 mg) | 19.4 | 61.2 | 3.5 | 20.9 |
| | | (100 mg) | 11.3 | 33.4 | 0 | 26.0 |
| | | (200 mg) | 27.2 | 51.7 | 13.4 | 33.2 |
| | +IV | (150 mg) | 0 | 41.7 | 11.1i | 14.7i |
| | | (300 mg) | 6.6i | 15.9 | 50.0i | 27.4i |
| | | (600 mg) | 3.1i | 47.1 | 9.6i | 27.4i |

Compound I and Lipitor were not effective in raising HDL-C. In this regard, combinations of I with fibrates and niacin were evaluated. Since niacin and existing fibrates are not soluble in water, sodium salts were prepared (Compounds II, III, and IV) and tested in combination with Compound I.

Table 4 shows the effect of Compound I (10 mg) combined with regular niacin and various fibric acid salts (150-600 mg). The niacin-Compound I combination resulted in decreased total cholesterol, LDL-C, and HDL-C, and increased triglycerides. On the other hand, Compound I combined with Compound IV (water soluble form) resulted in significant decrease in triglyceride levels, but increased levels of LDL-C, HDL-C, and total cholesterol.

In regard to Compound I (10 mg) combined with sodium fibrates (50-200 mg), Compound I and Compound III in combination yielded significant decreases in total cholesterol, triglycerides, HDL-C, and HDL-C; Compound I and II in combination yielded decreases in total cholesterol, triglyceride, LDL-C, and most interestingly significant increase in HDL-C (Table 3). Based on these data, it can be concluded that Compound I at the 8-160 mg range is as good or better than Lipitor in reducing cholesterol, triglyceride, and LDL-C. Compound I reduced LDL-C by 41.4-59.2% vs. 28.5-54.4% for Lipitor. On repeat experiment using 5-20 mg dose range, Compound I confirmed its antilipidemic activity, reducing LDL-C by 22.4-23.7% vs 8.9-17.9% for Lipitor. Compound I exhibited activity at doses as low as 5 mg. The four currently marketed statins (e.g., Lipitor, Mevacor, Zocor, Pravachol) in combination with Compound I did not show any increase in HDL-C. However, when Compound I (10 mg) was combined with Compound II (50-200 mg), HDL-C level was increased to 3.4-8.0. Compounds III or IV, combined with Compound I also resulted in increases in HDL-C level.

The results of the above examples confirm the claims for this invention that lovastatin, the parent compound is not water-soluble, while dihydroxy-acid sodium salt, referred to as Compound I is water-soluble. The parent compound fenofibrate is not water soluble but the sodium salt referred to as Compound II is water soluble. Compound I is more active than the prodrug lovastatin, where Compound I is almost 2-fold more active than the parent lovastatin in reducing total cholesterol and LDL-C. Compound I as monotherapy was effective in reducing total cholesterol, LDL-C, and triglyceride, and when combined with materials such as Compound II, a complementary additive therapeutic effect was observed not only by decreasing total cholesterol, LDL-C, triglyceride, but most importantly increasing the level of HDL-C at a relatively low dose levels and ranges.

EXAMPLE 5

Crestor is a new synthetic statin and considered "superstatin" because of its effectiveness at low doses. In clinical studies, Crestor is now found to be the new gold standard among the statins: a 5 mg Crestor dose is equivalent to 20 mg Lipitor, 40 mg Zocor, 80 mg Mevacor or Pravachol. Thus, the drug combination of Compound I and Compound II was compared with Crestor. The animal model was Syrian Golden hamsters ($F_1B$ strain, BioBreeders, Fitchburg Mass.). The animals approximately 8-10 weeks of age were fed a non-purified chow-based hypercholesterolemic diet (HCD) containing 10% coconut oil and 0.1% cholesterol by weight for 2 weeks prior to initiation of the experimental treatments, and remain on this diet for the remainder of the study. Compounds I and II were administered by oral gavage (0.2 mL), once a day for 14 days. At day 14, blood samples were obtained after an overnight fast.

Desirable overall lipid profile (i.e., decreased level of cholesterol, triglyceride, LDL, and elevated HDL) was achieved with combination formulations of Compounds I and II combo drugs (see Table 5). The effective doses found in this study were 1-3 mg of Compound I and 30-40 mg of Compound III. This drug combination showed superior lipid profile when compared with Crestor: Crestor did not boost HDL, level and was less effective in controlling cholesterol and LDL.

TABLE 5

Effect of Compounds I and II combo drugs on lipid profile compared with Crestor.

| | Type of Lipid/Percent increase (+) or decrease (−) | | | |
|---|---|---|---|---|
| Compound (dose)* | HDL | Cholesterol | LDL | Triglyceride |
| I (1-3 mg) + II (30-40 mg) | (+)8-35 | (−)3-19 | (−)11-32 | (−)11-44 |
| Crestor (3 mg) | (−)8-16 | (−)13-(+)16 | (−)19-(+)16 | (−)35-51 |

*mg/70 kg man.

EXAMPLE 6

It is known that toxicity associated with statins and fibrates include liver and kidney damage and muscle toxicity (rhabdomyolysis, myalgia, myopathy, and myositis). Thus, increasing dose combinations of Compounds I and II were tested in *Rattus norvegicus*, outbred Sprague Dawley (from Harlan) 10 rats/group (5 males and 5 females) to assess any associated toxicities. Age range at initiation of study was 8-14. Weight range at initiation of study was 225-250 gm. Quarantine/acclimation was one week. Animals were randomized to groups based on weight. Number per cage was 2-3. Environmental conditions: Conventional microisolator caging. Room temperature was maintained between 19 and 23° C. Relative humidify was maintained at 55-80%. The light/dark cycle was maintained on a 12 hour cycle. Animals were exposed to the test substance daily for 14 days (2 weeks); and the doses were administered by gavage.

Gross necropsy was performed in the animals in the study. Tissues were collected and examined for histopathology, e.g., liver, lung, heart (with aorta), thymus, lymph nodes, stomach, intestines, spleen, kidneys, adrenals, testes, ovaries, uterus, brain, and skeletal muscle. was determined by the state of autolysis at the time of examination. Collected tissues were placed in formalin overnight and then sectioned and cassetted the following day.

Blood samples were collected by cardiac puncture, 24 hours after the last treatment, as part of the necropsy protocol. Parameters examined include hematocrit (HCT), hemoglobin (Hgb), total erythrocyte count (RBC), total white cell count (WBC), differential count, and platelet estimate; calculated mean corpuscular volume (MCV), mean corpuscular hemoglobin (MCH), and mean corpuscular hemoglobin concentration (MCHC).

Also, at 16-18 hours after the last treatment, animals were placed in metabolic cages and urine was collected (just prior to necropsy). The urine samples were tested for presence of myoglobin.

Clinical Chemistry. Blood samples were collected by cardiac puncture, 24 hours after the last treatment, as part of the necropsy protocol. Clinical chemistries were performed on all animals from which blood was collected. Parameters examined included creatinine, alanine aminotransferase (ALT), alkaline phosphatase (ALK), creatine phosphokinase (CPK), and aldolase.

Results of this study provide reasonable evidence that the effective therapeutic combination of Compound I and Compound II (1-3 mg of Compound I and 30-40 mg of Compound II) is a relatively safe and effective to improve overall beneficial effect on all lipid abnormalities and possibly risk factors associated with coronary heart disease. As shown in Table 6, the "no-observable-adverse-effect-level (NOAEL)" for the combination of Compounds I and II is below 1000 mg for Compound II and 10,000 mg for Compound II. The dose of 1,000 mg Compound I and 10,000 mg Compound III can be considered the maximum tolerated dose (MTD). Combination therapy up to the MTD dose was well tolerated and no significant increases in serum liver and muscle enzymes were noticed. The level of the enzymes associated with toxicities in the liver (ALT, ALK), kidney (creatinine), and muscle function (CPK, aldolase) appeared normal up to the MTD level. Also, all urinalysis results were below 0.045 mg/dL of myoglobin, and hematology were within the normal range up to the MTD level.

TABLE 6

Toxicology profile of Compound I/II Combinations

| Compound I/II Combo** | CREATININE (MG/DL) | ALANINE NH₃TRANS (IU/L) | ALKALINE PHOS (IU/L) | CREATININE PHOS'KINASE (IU/L) | ALDOLASE (U/L) | HISTOPATHOLOGY |
|---|---|---|---|---|---|---|
| 20/200 | 0.4 | 48.0 | 142.0 | 312.0 | 22.0 | All tissues appear normal; no significant finding |
| 200/2000 | 0.4 | 56.0 | 205.0 | 364.0 | 26.0 | Skeletal muscle, no significant finding; heart, myocardial in one rat |
| 500/5000 | 0.5 | 64.7 | 236.7 | 488.6 | 52.3 | Cross sections of muscle fiber show some variation in size but believed to be artifactual since CPK is normal |
| 1000/10000 | 0.4 | 63.0 | 240.2 | 522.3 | 68.2 | Cross sections of muscle fiber show some variation in size but believed to be artifactual since CPK is normal |
| 2000/20000 | | | Toxic Dose | | | One surviving rat with clear damage |
| Control (Baseline) | 0.4 | 52.0 | 140.0 | 625.0 | 32.0 | All tissues appear normal |

*Liver function (liver enzymes): Alanine aminotransferase (ALT) and Alkaline phosphatase (ALK).
Kidney function: Creatinine
Muscle function (if animals appear affected with myositis): Creatinine phosphokinase (CPK), aldolase (ALD)
**mg/70 kg man.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A pharmaceutical composition comprising a therapeutically effective amounts of at least one HMG CoA reductase inhibitor present as a water soluble dihydroxy-open acid salt of a statin, the HMG CoA reductase inhibitor effective in lowering at least one of total cholesterol and/or LDL-C and at least one additional therapeutic agent exhibiting effects on at least one lipid abnormality presenting in a patient, wherein the at least one additional therapeutic agent raises HDL-C level in a patient wherein the water-soluble dihydroxy acid salt of a statin is a lactone prodrug having the general formula:

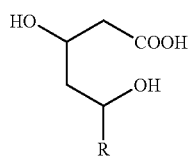

wherein R is a chromophore and wherein the statin is selected from the group consisting of lovastatin, simvastatin, pravastatin, fluvastatin, artorvastatin, cerivastatin, pitavastatin, rosuvastatin and mixtures thereof;

wherein the at least one additional therapeutic agent that raises HDL-C level in a patient is a water soluble fibrate derivative present in the free acid form, wherein the water soluble fibric acid derivative component is at least one of clofibrate, gemfibrozil, fenofibrate, bezafibrate, and ciprofibrate; and wherein the additional therapeutic agent further comprises is at least one of the following: a bile acid sequestrant, a nicotinic acid; or a bile acid sequestrant and a nicotinic acid.

2. A pharmaceutical composition comprising a therapeutically effective amounts of at least one HMG CoA reductase inhibitor present as a water soluble dihydroxy-open acid salt of a statin, the HMG CoA reductase inhibitor effective in lowering at least one of total cholesterol and/or LDL-C and at least one additional therapeutic agent exhibiting effects on at least one lipid abnormality presenting in a patient, wherein the at least one additional therapeutic agent raises HDL-C level in a patient, wherein the water-soluble dihydroxy acid salt of a statin is a lactone prodrug having the general formula:

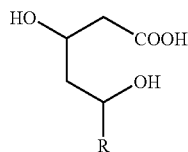

wherein R is a chromophore and wherein the statin is selected from the group consisting of lovastatin, simvastatin, pravastatin, fluvastatin, artorvastatin, cerivastatin, pitavastatin, rosuvastatin and mixtures thereof;

wherein the at least one additional therapeutic agent that raises HDL-C level in a patient is a water soluble fibrate derivative present in the free acid form, wherein the water soluble fibric acid derivative component is at least one of clofibrate, gemfibrozil, fenofibrate, bezafibrate, and ciprofibrate; and wherein the at least one additional therapeutic agent further is at least one of vitamin $B_6$, vitamin $B_{12}$, water soluble salts of folic acid, water soluble esters of folic acid, vitamin C, vitamin E, betacarotene and HIV protease inhibitors selected from the group consisting of indinavir, nelfinavir, ritinavir, and saquinavir.

3. The pharmaceutical composition of claim 1 wherein the HMG-CoA reductase inhibitor is a water-soluble dihydroxy acid salt of a statin.

4. The pharmaceutical composition of claim 1 wherein the salts of statin dihydroxy acids is at least one of the cation salts of sodium, potassium, aluminum, calcium, lithium, magnesium, zinc, and tetramethylammonium and amine salts including at least one of ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2,4,4-trimethyl-2-pentamine, and tris(hydroxymethyl)aminomethane.

5. The pharmaceutical composition of claim 4 wherein the salts of statin dihydroxy acids further comprises at least one ester derivatives including at least one of unsubstituted alkyls having 1 to 4 carbon atoms and substituted alkyls having 1 to 4 carbon atoms, wherein the substituted group is at least one of phenyl-dimethylamino- and acetylamino-groups.

6. The pharmaceutical of claim 5 wherein the alkyl group is one of methyl, ethyl, n-propyl, n-butyl, isopropyl, sec-butyl, and tert-butyl.

7. The pharmaceutical composition of claim 1 wherein the salts of fibric acid is at least one of cation salts of sodium, potassium, aluminum, calcium, lithium, magnesium, zinc, and tetramethylammonium and amine salts including at least one of ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'methylbenzimidazole, diethylamine, piperazine, morpholine,2,4, 4-trimethyl-2-pentamine, and tris(hydroxymethyl) aminomethane.

8. The pharmaceutical composition of claim 7 wherein the salts of fibric acid is composed of at least one ester derivative including at least one of unsubstituted alkyls having 1 to 4 carbon atoms and substituted alkyls having 1 to 4 carbon atoms, wherein the substituted group is at least one of phenyl-dimethylamino- and acetylamino-groups.

9. The pharmaceutical composition of claim 7 wherein the alkyl group is one of methyl, ethyl, n-propyl, n-butyl, isopropyl, sec-butyl, and tert-butyl.

10. The pharmaceutical of claim 1 wherein the bile acid sequestrant is at least one of cholestylramine, colestipol, and colesevelam.

11. The pharmaceutical of claim 1 wherein the niacin compound is nicotinic acid.

12. The pharmaceutical composition of claim 1 further comprises at least one HIV protease inhibitor selected from the group that includes at least one of indinavir, nelfinavir, ritinavir, and saquinavir.

13. The pharmaceutical of claim 1 wherein the HMG CoA reductase inhibitor and the additional therapeutic agent are formulated in an enteric coated dosage form wherein a substantial release of the compound from the dosage form after oral administration to a patient is delayed until passage of the dosage form through the stomach.

14. The pharmaceutical composition of claim 13 wherein the dosage form is surrounded by an enteric coating.

15. The pharmaceutical composition of claim 13 wherein the composition is formulated in an enterically coated rapid-release pharmaceutical dosage form.

16. The pharmaceutical composition of claim 13 wherein the composition is formulated in an enterically coated time controlled release pharmaceutical dosage form.

17. The pharmaceutical composition of claim 13 wherein the enteric coating is comprised of polyvinyl acetate phthalate, titanium dioxide, talc, colloidal silicon dioxide, triethyl citrate, polyethylene glycol, sodium bicarbonate, purified stearic acid, and sodium alginate.

18. The pharmaceutical composition of claim 1 wherein the HMG CoA reductase inhibitor present as a water soluble dihydroxy-open acid salt of rosuvastatin or simvastatin and at the additional therapeutic agent is at least one of clofibrate, gemfibrozil, fenofibrate, bezafibrate, and ciprofibrate.

* * * * *